United States Patent
Mbadugha

Patent Number: 5,876,378
Date of Patent: Mar. 2, 1999

[54] APPARATUS AND METHOD FOR INJECTING LIQUIDS INTO PATIENTS

[76] Inventor: Joseph O. Mbadugha, 115 Alford Rd., Lithonia, Ga. 30058

[21] Appl. No.: 962,995

[22] Filed: Nov. 2, 1997

Related U.S. Application Data

[63] Continuation of Ser. No. 717,183, Sep. 20, 1996, abandoned.

[51] Int. Cl.$^6$ ............................ A61M 1/00
[52] U.S. Cl. ..................... 604/152; 604/131; 604/65; 604/50
[58] Field of Search ..................... 604/151, 152, 604/154, 131, 27, 29, 30, 48, 65, 50; 364/413.01, 413.02, 413.03

[56] References Cited

U.S. PATENT DOCUMENTS

| | | | |
|---|---|---|---|
| 3,297,210 | 1/1967 | Lucas | 128/DIG. 1 |
| 3,335,724 | 8/1967 | Gienapp | 128/DIG. 1 |
| 3,731,674 | 5/1973 | Wilhelmson | 128/DIG. 1 |
| 4,059,110 | 11/1977 | Wuthrich | 128/218 |
| 4,409,966 | 10/1983 | Lambrecht | 128/1.1 |
| 4,620,848 | 11/1986 | Sutherland | 604/154 |
| 4,663,220 | 5/1987 | Hawryienko | 604/155 |
| 4,695,271 | 9/1987 | Goethel | 604/49 |
| 4,854,324 | 8/1989 | Hirschman et al. | 128/655 |
| 5,176,646 | 1/1993 | Kuroda | 604/151 |
| 5,254,096 | 10/1993 | Rondelet | 604/152 |
| 5,342,298 | 8/1994 | Michaels et al. | 604/65 |

*Primary Examiner*—Wynn Wood Coggins
*Assistant Examiner*—N. Kent Gring
*Attorney, Agent, or Firm*—Kennedy, Davis & Kennedy, P.C.

[57] ABSTRACT

A liquid metering and injecting device has a reservoir (10), a pump means (11) and a delivery tube (13) in fluid communication. A motor (19) of the pump means (11) is controllably operated so that a plunger (18) is reciprocated within a cylinder (17). A valve means (32) directs the flow of liquid from the reservoir (10) to the pump means (11) as the plunger (18) is retracted and from the pump means (11) to the delivery tube (13) as the plunger is extended without backflow. With this construction, a selected amount of liquid (14) is periodically metered and injected to a patient.

4 Claims, 2 Drawing Sheets

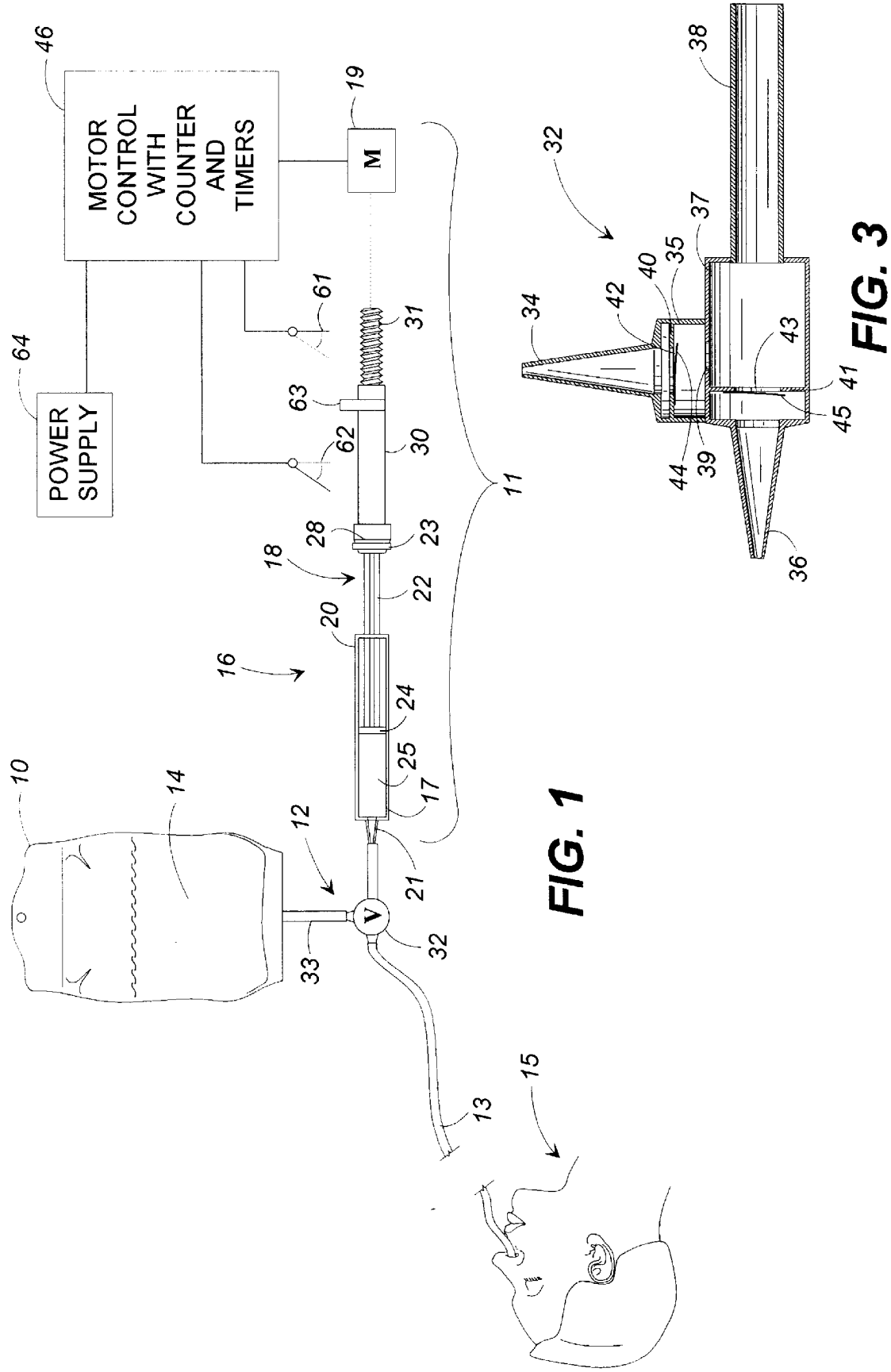

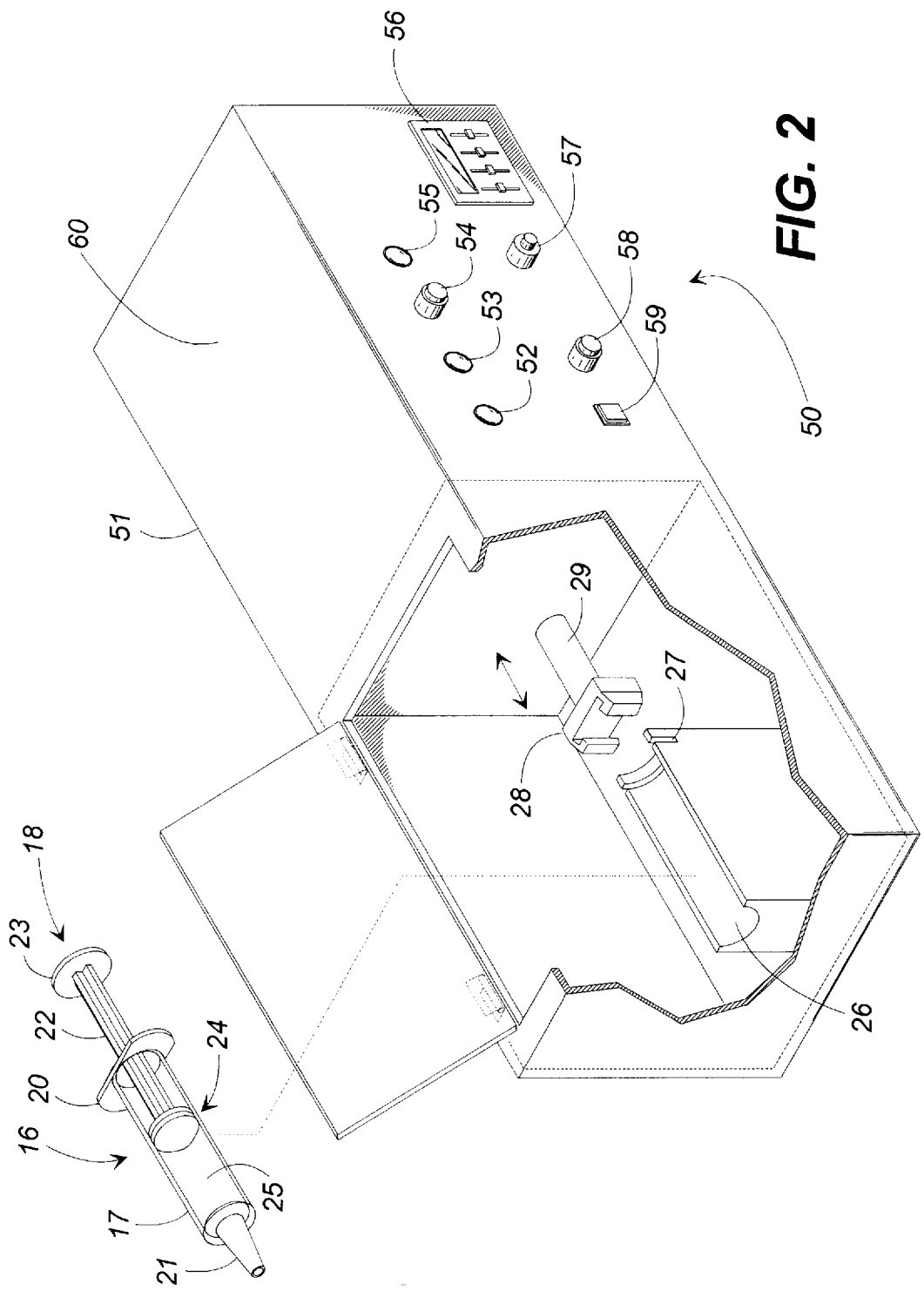

APPARATUS AND METHOD FOR INJECTING LIQUIDS INTO PATIENTS

This application is a continuation of application Ser. No. 08/717,183 filed on Sep. 20, 1996 now abandoned.

TECHNICAL FIELD

This invention relates generally to medical injection apparatuses and methods of injecting liquids into patients, and more particularly to apparatuses and methods for metering and injecting oral contrast media into patients through a nasogastric tube.

BACKGROUND OF THE INVENTION

In their simpler form, medical injection devices have comprised mechanically driven syringes wherein a clockwork mechanism, including a gear train, a mainspring, an escapement and a clutch, drives a syringe plunger. With such devices, fluid was preloaded into the syringe and delivered by injection to patients at controlled rates. An example of such devices is shown in U.S. Pat. No. 4,059,110.

Injection devices have also included electrical motors coupled to worm and spur gears for operating a spring driven syringe. An example of such devices is shown in U.S. Pat. No. 4,668,220. This type of device has been used primarily for controlling the delivery of preloaded fluid from a syringe to a patient over a long period of time.

Still others have incorporated features for electronically controlling the injection of preloaded fluid from a syringe to a patient. Such devices have electronically controlled the repeated delivery of partial amounts of fluid from a syringe, the time duration of the delivery, and the pressure of the fluid. Such devices have also been controlled so as to change the flow rates and pressures during the injection as desired, based on feedback information processed by computers.

In the above-described systems, the amount of fluid to be injected is preselected and loaded into the syringe. Thus, in existing devices the amount of fluid that can be injected at any one time, without reloading the syringe, is limited to the size of the syringe.

Apparatuses and methods for injecting oral contrast media into a patient through a nasogastric tube have been primarily limited to syringes operated by hand. For purposes of scanning selected organs or tissues by computed tomography ("CT") or by magnetic resonance imaging ("MRI"), oral contrast media is introduced into the patient's body in order to enhance the contrast of the particular organs or tissues to be viewed. Strict regulation of the rate of delivery of oral contrast media is particularly important so that the proper contrast and concentration of contrast fluid in the patient's body is achieved as prescribed by the attending physician for optimal viewing of the subject area and for acceptance of the contrast fluid by the patient's system. For example, in CT scans it has been found in practice that the desired concentration of oral contrast media is achieved by introducing the contrast fluid into the patient's nasogastric tube at a rate of one cup per ten minutes. Typically, the process of injection includes pre-loading a syringe with one cup of contrast fluid, injecting the same into the patient via a nasogastric tube, and repeating this process once every ten minutes until the desired amount of fluid is delivered. Of course, if a patient is conscious and able to swallow the contrast fluid, the desired concentration can be achieved by pouring a selected amount of fluid into a cup, bringing the cup to the patient's bedside, and repeating these tasks every ten minutes until the desired amount of fluid is transferred to the patient's system.

Oral contrast media typically contain barium or an iodinated contrast agent, both of which are difficult to ingest. If the oral contrast media is introduced to the patient's body at a rate faster than one cup per ten minutes, the patient is likely to reject the fluid from his or her body by vomiting.

Failure to adhere to a specified rate of delivery can also result in less than optimal viewing of the patient's internal organs through the scan. For instance, if delivered at a rate slower than that prescribed, or if vomited from the patient's body, a poor contrast may result due to the lower concentration of contrast fluid in the body.

Additionally, the likelihood for error in the manual delivery of oral contrast media to patients has been strong due to the human effort involved in measuring the amount of fluid to be delivered, in regulating the rate at which delivery is to occur, and in timing the repetitions of delivery. Where the patient is called upon to drink the fluid, or to monitor his or her own delivery of fluid, the possibility of error on the part of the patient is present as well as that of the nurse. The possibility for error on the part of the patient may be further increased depending on how the patient's judgment is effected by the injury or illness under which the patient is suffering. Likewise, the possibility for error on the part of the nurse is enhanced where the nurse is not able to devote full attention to the delivery of the fluid during the delivery period due to the number of patients he or she may be caring for, to the number of additional tasks he or she may be simultaneously performing, or to interruptions in the nurse's duties due to a more important matter arising such as an emergency situation concerning another patient. One example of such multiple tasks a nurse often performs simultaneously is the preparation of a patient for a CT or MRI scan, including achieving proper concentration of contrast media within the desired viewing area of the patient's body, while concurrently monitoring the progress of at least one other patient already prepared and undergoing a CT or MRI scan. The possibility of human error is also present when using known devices requiring manual pre-loading of fluid into syringes and manual timing of repeated injections.

Accordingly, it is seen that a need remains for an injection apparatus and method that periodically meters a selected amount of fluid from a reservoir rather than a syringe and injects that fluid into a patient at a desired rate repeating such metering and injecting as needed to transfer a desired amount of fluid to a patient. It is also seen that a need remains to reduce the possibility of human error caused by manually pre-loading, delivering, and timing repeated doses of oral contrast media to a patient at a desired rate. It is to the provision of such therefore that the present invention is primarily directed.

SUMMARY OF THE INVENTION

In a preferred form of the invention, an apparatus for injecting liquid into a patient comprises a reservoir for holding a supply of liquid, a delivery tube, and a pump means for pumping liquid from the reservoir through the delivery tube to the patient. The pump means comprises a cylinder, a plunger mounted for reciprocation within the cylinder, and a motor for reciprocating the plunger between retracted and extended positions.

Conduit means are provided for establishing fluid communication between the reservoir, the pump means and the delivery tube. Valve means are provided for directing liquid from the reservoir toward the pump means as the plunger is retracted and for directing liquid from the pump means toward the delivery tube as the plunger is extended. With this construction, a predetermined amount of liquid may be periodically drawn from the reservoir and pumped through the delivery tube to a patient.

Preferably the pump means is in the form of a syringe having a selected displacement volume and a plunger. A motor is coupled to the plunger and controlled to meter and inject a selected number of units of the displacement volume of liquid into the delivery tube and the patient.

In another preferred form of the invention, a method for periodically metering and injecting liquid into a patient comprises establishing fluid communication between a reservoir, a syringe and a delivery tube. The plunger of the syringe is then coupled to a reversible drive motor and cyclically driven to meter and inject liquid into the delivery tube and the patient.

BRIEF DESCRIPTION OF THE DRAWINGS

FIG. 1 is a schematic view of a liquid injection apparatus embodying principles of the invention shown in use and in practicing the method of the invention.

FIG. 2 is a perspective view of a portion of the apparatus shown schematically in FIG. 1.

FIG. 3 is a sectional view of the valve shown in FIG. 1 as V.

DETAILED DESCRIPTION

With reference to the drawings, there is shown in FIG. 1 a reservoir 10, a pump 11, a conduit 12 and a delivery tube 13. The reservoir 10 is comprised of a transparent plastic bag of a type typical of those used in hospitals to infuse liquid to patients intravenously. The reservoir holds a supply of liquid 14 to be injected into the patient 15.

The pump 11 is comprised of a conventional syringe 16 having a cylinder 17 and a plunger 18. An electric motor 19 is provided for reciprocating the plunger. As best shown in FIG. 2, the cylinder 17 has a lip 20 on one end and a spout 21 on the other end. The plunger 18 has a rod 22 with a disc-shaped head 23 on one end and a rubber gasket 24 on the other end. A chamber 25 is formed within the cylinder between the gasket 24 and the spout 21.

The pump 11 also includes a cradle 26 for removably holding the syringe 16. The cradle has a notch 27 for receiving the cylinder lip 20. A coupling 28 is provided on one end of a drive shaft 29 for receiving the head 23 of the plunger rod 22. The drive shaft 29 includes an internally threaded sleeve 30 for receiving a threaded rod 31, shown in FIG. 3, to which the motor 19 is rotatably coupled. The motor 19 drives the shaft to reciprocate the plunger 18 within the cylinder 17 between retracted and extended positions as the cylinder is held in place in the cradle.

The conduit 12 is comprised of a plastic tubing network 33 that provides fluid communication between the reservoir 10, the pump 11 and the delivery tube 13. A valve 32 is positioned within the plastic tubing network. As best shown in FIG. 3, the valve 32 has an entrance nozzle 34, an entrance chamber 35, an exit nozzle 36, an exit chamber 37, and a central channel 38. A plastic tube 33 extends from the reservoir 10 to the entrance nozzle 34 of the valve. The central channel 38 of the valve is adapted to receive the spout of the cylinder. The exit chamber has an opening 39 in its side separating the entrance and exit chambers. Positioned within each chamber is a diaphragm 40, 41 having a hole 42, 43 and a flexible rubber flap 44, 45 for covering one side of the hole.

The delivery tube 13 is comprised of plastic tubing and is adapted to receive the exit nozzle 36 in one end. The opposite end of the delivery tube is inserted in the patient 15 typically through a nostril into his or her stomach.

The apparatus also includes a controller 46 having a control panel 50, shown in FIG. 2, including a power lamp 52, an injection lamp 53, a buzzer 54, a buzzer lamp 55, a counter 56, a reset switch 57, a start switch 58, and an on/off switch 59. The power lamp 52 is a colored bulb that illuminates when the on/off switch 59 is pressed to indicate that electrical power is flowing from the power supply 64 to the controller. The injection lamp 53 is also a colored bulb, but of a different color than the power lamp 52. The injection lamp 53 illuminates when the start switch 58 is pressed and the motor 19 is extending or retracting the plunger 18.

The counter 56 is provided for setting and counting the total time of operation of the motor for delivery of a desired amount of liquid 14 from the reservoir to the patient. The counter is a Programmable Multifunction Time Delay Relay/Counter made by Potter & Brumfield, CNT-35-26 having five thumbwheel settings. The first thumbwheel determines the function the counter will perform. It is preferred that the first thumbwheel remain set on the letter "A" to perform the function of "Delay On Operate". The fifth thumbwheel indicates units of time in seconds, minutes and hours and fractions thereof. The second, third and fourth thumbwheels indicate, in numeric digits, the amount of time desired in terms of the units selected for the first thumbwheel. The following chart indicates the time settings for metering and injecting up to seven cups of oral contrast media if all preferred parameters herein are used:

| Total Amount for Transfer | | Time for Transfer | Thumbwheel Settings |
| --- | --- | --- | --- |
| 1 cup  | = | 107 seconds  | A 1 0 7 (S*) |
| 2 cups | = | 800 seconds  | A 8 0 0 (S) |
| 3 cups | = | 24.8 minutes | A 2 4 8 (.1m**) |
| 4 cups | = | 36.8 minutes | A 3 6 8 (.1m) |
| 5 cups | = | 49 minutes   | A 4 9 0 (.1m) |
| 6 cups | = | 60.2 minutes | A 6 0 2 (.1m) |
| 7 cups | = | 72 minutes   | A 7 2 0 (.1m) |

*S is seconds.
**.1m is 1/10 of a minute.

The buzzer lamp 55 is a colored bulb of a color other than the colors of the power lamp and the injection lamp. The buzzer lamp 55 is illuminated and the buzzer 54 is sounded when operation of the pump is completed. The reset switch 57 is a button that turns off the buzzer 54. The electrical circuitry of the controller 46 is mounted within the enclosed portion 60 of the housing 51.

As shown in FIG. 1, limit switches 61, 62 are provided for maintaining plunger movement within the cylinder 17 while the syringe is positioned in the cradle 26. The limit switches are inversely biased against one another so that one is normally opened while the other is normally closed. The limit switches are connected to the motor 19 such that when current is flowing through one limit switch the motor rotates the threaded rod 31 in one direction and when current is flowing through the other limit switch the motor rotates the threaded rod 31 in the other direction. The limit switches are triggered to reverse the rotation of the motor 19 when the contact 63 mounted on the sleeve 30 contacts either of the limit switches. In this manner, electrical current flows to the motor through one limit switch or the other to operate the motor.

The controller 46 also has a reciprocation timer and an interval timer. The reciprocation timer controls the length of time the motor operates to continuously reciprocate the plunger 18. The interval timer controls the length of time between the beginning of each interval of continuous reciprocation.

In operation, the pump is first prepared by placing the plunger 18 within the cylinder 17 to form a chamber 25 between the gasket 24 and the spout 21. The cylinder is positioned within the cradle 26 while the lip 20 is nested into the notch 27 and the head 23 of the plunger 18 is inserted into the coupling 28 attached to the sleeve 30 of the drive shaft 29. With the cylinder and plunger in place, the spout 21 of the cylinder protrudes through an unshown opening in the housing 51 so that the spout is accessible for attachment to the central channel 38 of the valve 32.

The conduit 12 is then assembled by attaching the plastic tubing 33 to the reservoir 10 and to the entrance nozzle 35 of the valve 32, and by attaching the cylinder spout 21 to the central channel 38, and by attaching the exit nozzle 36 to the delivery tube 13. Such assembly places the reservoir 10, the pump 11 and the delivery tube 13 in fluid communication.

The desired settings for the controller are then selected and the start button 58 is pressed to begin injection. It is preferred that the shaft 29 is in an extended position when the start button is pressed so that the pump 11 will begin drawing the liquid 14 from the reservoir 10 immediately. It is also preferred that the system is primed when the start button is pressed so that air is not pumped through to the patient along with the liquid. Such priming can be accomplished by connecting the entrance nozzle 34 of the valve 32 to a reservoir of liquid and manually pumping the plunger 18 several times until the media exits through the exit nozzle 36 of the valve.

Once started, the motor 19 reciprocates the plunger 18 between the desired retraction and extension points as maintained by the limit switches 16, 62. As the plunger is drawn, liquid 14 is metered from the reservoir 10 to the pump 11. As the liquid flows through the entrance nozzle 35 to the exit chamber 37, the rubber flap 44 of the entrance diaphragm 40 is pushed away from the hole 42 to allow the liquid to pass through the entrance chamber 35 into the exit chamber 37. Once the contact 63 contacts the forward limit switch 61, the rotation of the motor is reversed such that the plunger is driven forward to inject the metered liquid into the patient. As the metered liquid is injected through the valve 32, the rubber flap 44 is pushed to a closed position so that hole 42 is covered thereby preventing backflow toward the reservoir 10. Also as the metered liquid is injected, the exit diaphragm 41 is pushed open to allow the metered liquid to flow from the exit chamber 37 through the exit nozzle 36 to the delivery tube 13.

Continuous reciprocation of the plunger 18 occurs for the time allowed by the reciprocation timer. Each interval of continuous reciprocation begins according to the time limitation set by the interval timer. A sequence of intervals of continuous reciprocation occurs for the duration of time provided by the counter 56. Once the duration of time provided by counter 56 expires, the motor will stop, the buzzer 54 will sound, and the buzzer lamp 55 will flash to alert the attending medical personnel that the desired amount of liquid 14 has been metered from the reservoir 10 and injected into the patient 15. When the motor stops, the plunger is in approximately the same position from which it began. If in the preferred position, it will be extended and thereby in proper position for the next injection.

In the preferred embodiment, the reservoir 10 is comprised of a 1500 ml bottle of oral contrast media. The syringe 16 has a selected displacement volume of 60 cubic centimeters. The motor 19 is made by Hurst, Princeton, Ind. having the following part descriptions engraved on it: 360 RPM, Model PB, 115 Volt, 60 Hz, 10 W, and P/N 3204-033. The reciprocation and interval timers are AGASTAT® timing relays, Cat. No. SST12AGA, Volt: 120 VAC, Time: 18 Sec. - 30 Min., made by Industrial Electrical Products, Amerace Corporation, Livingston, N.J. 07039.

With the above-specified motor, syringe and timers, it has been found in practice that the apparatus will meter and inject approximately one cup of liquid if the reciprocation timer is set for about three and one-half minutes. With the interval timer set at approximately ten minutes and the thumbwheels of the counter 56 set according to the counter chart provided herein, it has been found in practice that the apparatus will repeat its continuous reciprocation every ten minutes to meter and inject a selected number of cups of liquid to the patient.

It thus is seen that a new liquid injection apparatus is now provided that overcomes problems long associated with those of prior art. It should be understood however that many modifications, additions and deletions may be made thereto without departure from the spirit and scope of the invention as set forth in the following claims.

I claim:

1. An apparatus for metering doses of liquid into the stomach of a patient comprising a reservoir for holding a supply of the liquid, a pump means including a syringe having a selected liquid displacement volume and a plunger, and an electric motor means for cyclically driving said plunger, a delivery tube through which fluid may be delivered to the stomach, valve means for directing the liquid from said reservoir to said pump means as said plunger is retracted and from said pump means to said delivery tube as said plunger is extended, and control means for repeatedly operating said pump means for repeated periods of injection separated by periods of non-injection to meter doses of fluid from said reservoir into the stomach while allowing the patient time in which to digest the metered doses.

2. The apparatus of claim 1 wherein said control means further includes a timing means for controlling a duration of engagement of said motor means and a duration of disengagement of said motor means.

3. The apparatus of claim 2 wherein said timing means further controls a sequence of engaging and disengaging plunger movement.

4. A method for metering units of liquid from a reservoir and spacing apart deliveries of the metered units to a patient through a delivery tube comprising the steps of:

(a) establishing fluid communication between a syringe having a selected liquid displacement volume, a reservoir of liquid and a delivery tube, (b) coupling the syringe plunger with a reversible drive motor, and (c) cyclically engaging the motor to drive the syringe plunger a pre-selected number of cycles to meter and deliver a desired amount of liquid into a patient and disengaging the motor for a predetermined time interval to space apart the delivered liquid from subsequent deliveries.

* * * * *